US008877161B2

(12) United States Patent
Yu et al.

(10) Patent No.: US 8,877,161 B2
(45) Date of Patent: Nov. 4, 2014

(54) GM1-LIKE PEPTIDES AND USES THEREOF

(71) Applicant: Georgia Regents Research Institute, Inc., Augusta, GA (US)

(72) Inventors: Robert Yu, Augusta, GA (US); Han-Chung Wu, Taipei (TW)

(73) Assignee: Georgia Regents Research Institute, Inc., Augusta, GA (US)

( * ) Notice: Subject to any disclaimer, the term of this patent is extended or adjusted under 35 U.S.C. 154(b) by 0 days.

(21) Appl. No.: 13/655,767

(22) Filed: Oct. 19, 2012

(65) Prior Publication Data

US 2013/0115170 A1 May 9, 2013

Related U.S. Application Data

(60) Provisional application No. 61/549,014, filed on Oct. 19, 2011.

(51) Int. Cl.

| | |
|---|---|
| ***C07K 7/08*** | (2006.01) |
| ***A61K 49/00*** | (2006.01) |
| ***A61K 38/10*** | (2006.01) |
| ***A61K 45/06*** | (2006.01) |

(52) U.S. Cl.

CPC . *C07K 7/08* (2013.01); *A61K 38/10* (2013.01); *A61K 45/06* (2013.01); *A61K 49/00* (2013.01)

USPC ............ 424/9.1; 530/327; 514/21.5; 514/2.3; 514/17.7; 514/2.8

(58) Field of Classification Search

None

See application file for complete search history.

(56) References Cited

U.S. PATENT DOCUMENTS

| | | | |
|---|---|---|---|
| 4,016,100 | A | 4/1977 | Suzuki |
| 4,235,871 | A | 11/1980 | Papahadjopoulos |
| 4,485,054 | A | 11/1984 | Mezei |
| 4,761,288 | A | 8/1988 | Mezei |
| 4,853,228 | A | 8/1989 | Wallach |
| 5,013,497 | A | 5/1991 | Yiournas |
| 5,474,848 | A | 12/1995 | Wallach |
| 5,628,936 | A | 5/1997 | Wallach |
| 5,653,996 | A | 8/1997 | Hsu |

OTHER PUBLICATIONS

Bowie et al (Science, 1990, 257:1306-1310).*

Colman (Res. Immunology, Jan. 1994, vol. 145, pp. 33-36).*

Greenspan et al. (Nature Biotechnology 7: 936-937, 1999).*

Abrahmsen, et al., "Engineering subtilisin and its substrates for efficient ligation of peptide bonds in aqueous solution", Biochemistry, 30:4151-9 (1991).

Callow, et al., "Thermodynamic modeling and cryomicroscopy of cell-size, unilamellar, and paucilamellar liposomes", Cryobiology, 22(3):251-67 (1985).

Dawson, et al., "Synthesis of Proteins by Native Chemical Ligation", Science, 266:776 9 (1994).

Kim, et al., "Preparation of multivesicular liposomes", Biochim Biophys Acta., 728:339-8 (1983).

Roberts, et al., "Chemistry for peptide and protein PEGylation", Adv Drug Deliv Rev., 54:459-76 (2002).

Tkachenko, et al., "Multifunctional gold nanoparticle-peptide complexes for nuclear targeting", J Am Chem Soc, 125:4700-1 (2003).

* cited by examiner

*Primary Examiner* — Robert A Zeman

(74) *Attorney, Agent, or Firm* — Pabst Patent Group LLP

(57) ABSTRACT

Compositions and methods relating to interfering with the interaction of gangliosides, such as GM1, with their ligands are provided. For example, methods are provided for treating infections by blocking the infectious agent from binding with GM1 using GM1-like peptides. Also provided are methods of inhibiting ligands from binding to GM1 on the surface of cells and for neutralizing anti-GM1 antibodies in neurological diseases.

6 Claims, 2 Drawing Sheets

GM1-LIKE PEPTIDES AND USES THEREOF

CROSS REFERENCE TO RELATED APPLICATIONS

This application claims priority to and benefit of U.S. Provisional Application No. 61/549,014 filed Oct. 19, 2011, and where permissible is incorporated herein in its entirety.

STATEMENT REGARDING FEDERALLY SPONSORED RESEARCH OR DEVELOPMENT

This invention was made with Government Support under Agreement USPHS RO1 NS26994-21 awarded to Robert Yu by the National Institutes of Health. The Government has certain rights in the invention.

REFERENCE TO SEQUENCE LISTING

The Sequence Listing submitted Oct. 19, 2012 as a text file named "GHSU_2012_004_Sequence_Listing.txt," created on Oct. 18, 2012, and having a size of 1,671 bytes is hereby incorporated by reference pursuant to 37 C.F.R. §1.52(e)(5).

FIELD OF THE INVENTION

The invention is generally related to peptides that interfere, inhibit, or block binding of ganglioside epitopes, particularly epitopes of GM1, and methods of using the peptides to treat ganglioside-mediated disorders.

BACKGROUND OF THE INVENTION

Ganglioside GM1-associated diseases or infections are prevalent world-wide, and hundreds of millions of people are infected, or diagnosed, with ganglioside GM1-associated diseases each year. Exemplary diseases or disorders involving GM1 include, but are not limited to Guillain-Barré Syndrome (GBS), lupus, cholera, and enterotoxigenic *Escherichia coli* (ETEC) infection. Unfortunately, existing treatments for disorders involving GM1 are limited and often have undesirable side-effects.

For example, conventional treatment strategies for GBS rely heavily on the removal of pathogenic anti-glycolipid antibodies (anti-GM1 antibodies) from the blood. In practice, plasmapheresis and intravenous immunoglobulin (IVIG) have been used extensively for treatment (Buchwald et al, Ann Neurol, 51: 673-680 (2002); Kieseier et al., Curr Opin Neurol, 21: 555-562 (2008)). Both strategies, however, are invasive and remove both nonpathogenic and pathogenic antibodies from circulation, can be painful, and with attendant risk of undesirable side effects including severe anaphylactoid reactions.

Existing cholera treatments such as vaccines are expensive and require complex logistics for distribution. Many countries where cholera is endemic cannot afford even the cheapest of the currently existing cholera vaccines. Due to instability of current vaccine formulations, a temperature-controlled system for distribution is required. Such a requirement increases the cost of cholera vaccines.

The current therapy for ETEC is to initiate treatment with agents such as antidiarrheals, rehydration therapy, and combinations thereof. The majority of the treatments involve the non-specific removal of the toxins from the intestinal tract. Only in moderate to severe cases of diarrhea where distressing or incapacitating symptoms are reported is antimicrobial therapy recommended. ETEC is frequently resistant to common antibiotics such as trimethoprim-sulfamethoxazole and ampicillin. Antibiotics are not usually effective at reducing clinical symptoms of the disease and problems associated with antibiotic resistance can occur. Prophylactic use of antibiotics is not recommended.

Therefore, it is an object of the invention to provide methods and compositions for treating GM1-associated diseases, including cholera, ETEC and GBS.

It is another object of the invention to provide methods and compositions for blocking, inhibiting, or reducing binding of GM1.

SUMMARY OF THE INVENTION

Compositions that inhibit or block ligand binding to GM1 and methods of their use are provided. Preferred compositions include peptides that inhibit or block ligand binding under physiologic conditions to GM1 in a subject. Exemplary inhibitory peptides form a three dimensional structure under physiological conditions that mimics a ligand binding site of GM1.

One embodiment provides peptides having a sequence that includes the amino acids of SEQ ID NO:1 (VSWKTWFPNLAV), SEQ ID NO:2 (YSPFHKWFPSMH), SEQ ID NO:3 (IPQVWRDWFKLP), SEQ ID NO:4 (FPAWFTKLYPRT), SEQ ID NO:5 (QINTAKWWKTHF), or SEQ ID NO:6 (DASKALRSSGMP). The peptides optimally include one or more conservative amino acid substitutions. The peptides can be formulated as pharmaceutical compositions optionally combined with one or more additional therapeutic agents.

Another embodiment provides a method for treating a GM1-mediated disease or disorder by administering to a subject an effective amount of one or more of the disclosed peptides to the subject to inhibit, reduce, or block ligand binding of GM1 in the subject. GM1 ligands include, but are not limited to proteins including peptides including bacterial or fungal proteins and toxins as well as antibodies to GM1. The disclosed peptides can also inhibit, reduce or block signal transduction mediated by or through GM1 or a GM1 receptor by inhibiting, reducing, or blocking ligand interaction of GM1.

Still another embodiment provides a method for treating bacterial infection in a subject by administering to the subject an effective amount of a peptide that inhibits, reduces, or blocks binding of bacterial ligand to GM1 in the subject. Preferred peptides include peptides containing the amino acid sequence of SEQ ID NO:1, SEQ ID NO:2, SEQ ID NO:3, SEQ ID NO:4, SEQ ID NO:5, or SEQ ID NO:6, optionally with one or more conservative amino acid substitutions. Representative bacterial infections that can be treated include, but are not limited to ETEC infection.

Yet another embodiment provides a method for treating a GM1-mediated autoimmune disorder by administering to a subject an effective amount of the disclosed peptides to inhibit, reduce, or block binding of auto-antibodies to GM1 in the subject. Preferred GM1-mediated autoimmune disorders include, but are not limited to GBS.

The compositions include peptides that bind or are bound by cholera toxin, preferably the B subunit, ETEC B subunit, or anti-GM1 antibodies. The disclosed peptides can bind all of these, one of these or a combination thereof.

The disclosed peptides can be modified to increase bioavailability or to increase or maintain the half-life of the peptides using methods known in the art. For example, one or more of the peptides can be modified with polyethyleneglycol (pegylated). Fusion proteins containing the disclosed peptides are also provided.

DETAILED DESCRIPTION OF THE INVENTION

Figure 1:
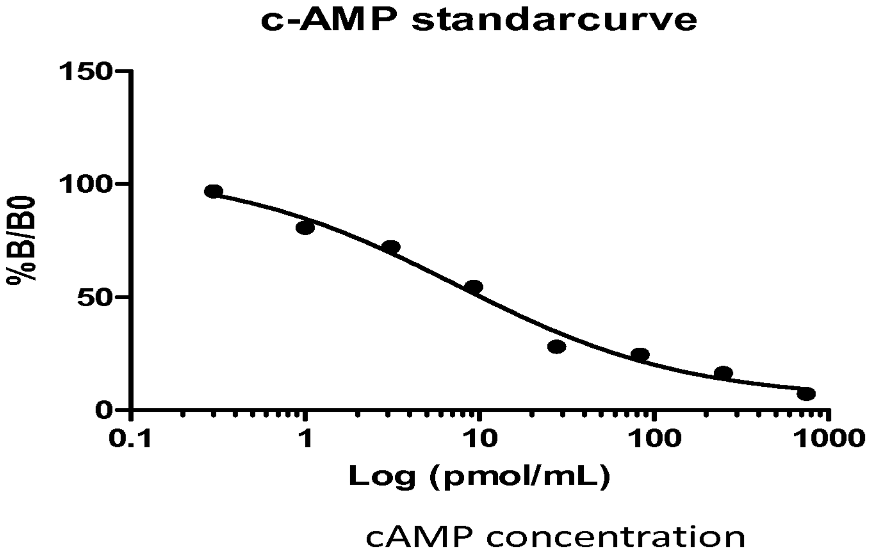
FIG. 1 is a line graph of cAMP concentration (Log(pmol/mL)) versus % $B/B_0$. The graph shows the standard curve for cAMP.

The disclosed materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a peptide is disclosed and discussed and a number of modifications that can be made to a number of molecules including the peptide are discussed, each and every combination and permutation of peptide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

I. DEFINITIONS

A "chimeric molecule" is a single molecule created by joining two or more molecules that exist separately in their native state. The single, chimeric molecule can have the desired functionality of all of its constituent molecules. In some instances, the chimeric molecule has altered functionality. The altered functionality can be an increase or decrease in the normal functionality. It can also be the functionality of only one of the molecules. Frequently, one of the constituent molecules of a chimeric molecule is a "targeting molecule" or "targeting moiety." The targeting molecule is a molecule such as a ligand or an antibody that specifically binds to its corresponding target, for example a receptor on a cell surface A "disease agent" or "infectious agent" is an element or agent of the disease or infection that is involved in the pathology of the disease or infection. A disease agent or infectious agent plays a role in the disease. For example, disease agents or infectious agents can be antibodies or proteins.

The term "effective amount" or "therapeutically effective amount" means a dosage sufficient to provide treatment of the disease, disorder, infection, or condition being treated, to inhibit or reduce ligand binding to GM1 to provide a desired pharmacologic or physiologic effect. The precise dosage will vary according to a variety of factors such as subject-dependent variables (e.g., age, etc.), the disease, and the treatment being effected.

The term "effector molecule" refers to a substance that acts upon target cell(s) or tissue to bring about a desired effect. The effect can, for example, be the labeling, activating, repressing, or killing of the target cell(s) or tissue. The effector molecule can be a small molecule, pharmaceutical drug, toxin, fatty acid, detectable agent, conjugating tag, nanoparticle, or enzyme.

A "fusion protein" refers to a peptide, polypeptide, protein or peptide mimetic formed by joining two or more polypeptides or peptide mimetics. Fusion proteins can be prepared using conventional techniques in molecular biology to join the two genes in frame into a single nucleic acid, and then expressing the nucleic acid in an appropriate host cell under conditions in which the fusion protein is produced.

The term "liposome" refers to a structure having an outer lipid bi- or multi-layer membrane.

The term "nucleic acid" refers to a natural or synthetic polymer of natural or non-natural nucleotides. Two or more nucleotides are typically linked by a phosphate group at the 3' position of one nucleotide to the 5' end of another nucleotide. The nucleic acid is not limited by length and can include deoxyribonucleic acid (DNA), ribonucleic acid (RNA), or combinations thereof.

The term "operably linked to" refers to the functional relationship of a nucleic acid with another nucleic acid sequence. Promoters, enhancers, transcriptional and translational stop sites, and other signal sequences are examples of nucleic acid sequences operatively linked to other sequences. For example, operative or operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

Unless the context indicates otherwise, reference herein to "peptide" is intended to refer to amino acid segments, which can form a part of, or constitute an entire, peptide. "Peptide" and "polypeptide" can be used interchangeably. Peptide is used broadly to mean peptides, proteins, fragments of proteins, and the like. A GM1-like peptide is a peptide that resembles, but is not identical to, an amino acid sequence of GM1.

The term "peptide mimetic" or "peptidomimetic" refers to a peptide-like molecule that emulates a sequence derived from a protein or peptide. A peptide mimetic or peptidomimetic can contain amino acids as well as non-amino acid components. Some may not contain any amino acids. A GM1 peptide mimetic mimics a portion of the GM1 ganglioside sequence.

The term "subject", "individual" or "patient" refers to any individual who is the target of administration. The subject can be a vertebrate, for example, a mammal. Thus, the subject can be a human.

By "treatment" and "treating" is meant the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

The term "vector" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element). "Plasmid" and "vector" are used interchangeably, as a plasmid is a commonly used form of vector. Moreover, the disclosed vectors include other vectors which serve equivalent functions.

The term "ganglioside-like peptides" refers to a peptide that resembles, but is not identical to, a ganglioside or ganglioside epitope.

The term "GM1-Like Peptides" refers to a peptide that resembles, but is not identical to, GM1 or a GM1 epitope.

The term "GM1 ligand binding domain" refers to a peptide, a region of a peptide, or a region of a molecule that is capable of binding a GM1 ligand, such as cholera or GM1 antibodies.

II. COMPOSITIONS THAT INTERFERE WITH LIGAND BINDING OF GM1 GANGLIOSIDE

Exemplary compositions that interfere with ligand binding to GM1 include peptides containing one or more GM1 ligand binding domains. The peptides include non-naturally occurring GM1-like peptides and GM1 mimetics. GM1-like peptides can be any amino acid sequence that is not identical to GM1 but mimics a particular sequence, epitope, or ligand binding domain of GM1. For example, the disclosed peptides can mimic a carbohydrate epitope of GM1.

In some embodiments, a peptide having the GM1 ligand binding domain can have an amino acid sequence at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequences SEQ ID NO:1, SEQ ID NO:2, SEQ ID NO:3, SEQ ID NO:4, SEQ ID NO:5, or SEQ ID NO:6. In some forms, the disclosed peptides consist of the amino acid sequences of SEQ ID NO:1, SEQ ID NO:2, SEQ ID NO:3, SEQ ID NO:4, SEQ ID NO:5, or SEQ ID NO:6.

A. Peptides

The disclosed peptides that contain a GM1 ligand binding domain are also referred to as peptidomimetics of GM1. The disclosed peptides can be in isolated form. As used herein in reference to the disclosed peptides, the term "isolated" means a peptide that is in a form that is relatively free from material such as contaminating polypeptides, lipids, nucleic acids and other cellular material that normally is associated with the peptide in a cell or that is associated with the peptide in a library or in a crude preparation.

The disclosed peptides can have any suitable length sufficient to bind to GM1 ligands. The disclosed peptides can have, for example, a relatively short length of less than six, seven, eight, nine, ten, 12, 15, 20, 25, 30, 35, 40 or 50 residues, preferably consecutive amino acids of SEQ ID NOs:1-6. The disclosed peptides also can be useful in the context of a significantly longer sequence. Thus, the peptides can have, for example, a length of up to 20, 30, 40, 50, 100, 150, 200, 250, 300, 400, 500, 1000 or 2000 residues. In particular embodiments, a peptide can have a length of at least 10, 20, 30, 40, 50, 60, 70, 80, 90, 100 or 200 residues. In further embodiments, a peptide can have a length of 5 to 200 residues, 5 to 100 residues, 5 to 90 residues, 5 to 80 residues, 5 to 70 residues, 5 to 60 residues, 5 to 50 residues, 5 to 40 residues, 5 to 30 residues, 5 to 20 residues, 5 to 15 residues, 5 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues. As used herein, the term "residue" refers to an amino acid or amino acid analog.

The disclosed amino acid segments can have, for example, a relatively short length of less than six, seven, eight, nine, ten, 12, 15, 20, 25, 30, 35 or 40 residues. The disclosed amino acid segments also can be useful in the context of a significantly longer sequence. Thus, the amino acid segments can have, for example, a length of up to 50, 100, 150, 200, 250, 300, 400, 500, 1000 or 2000 residues. In particular embodiments, an amino acid segment can have a length of at least 10, 20, 30, 40, 50, 60, 70, 80, 90, 100 or 200 residues. In further embodiments, an amino acid segment can have a length of 5 to 200 residues, 5 to 100 residues, 5 to 90 residues, 5 to 80 residues, 5 to 70 residues, 5 to 60 residues, 5 to 50 residues, 5 to 40 residues, 5 to 30 residues, 5 to 20 residues, 5 to 15 residues, 5 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues. As used herein, the term "residue" refers to an amino acid or amino acid analog.

1. Peptide Variants and Derivatives

The disclosed peptides and amino acid segments can be modified. As an example, a "methylated derivative" of a protein, peptide, amino acid segment, amino acid sequence, etc. refers to a form of the protein, peptide, amino acid segment, amino acid sequence, etc. that is methylated. Unless the context indicates otherwise, reference to a methylated derivative of a protein, peptide, amino acid segment, amino acid sequence, etc. does not include any modification to the base protein, peptide, amino acid segment, amino acid sequence, etc. other than methylation. Methylated derivatives can also have other modifications, but such modifications generally will be noted. For example, conservative variants of an amino acid sequence would include conservative amino acid substitutions of the based amino acid sequence. Thus, reference to, for example, a "methylated derivative" of a specific amino acid sequence "and conservative variants thereof" would include methylated forms of the specific amino acid sequence and methylated forms of the conservative variants of the specific amino acid sequence, but not any other modifications of derivations. As another example, reference to a methylated derivative of an amino acid segment that includes amino acid substitutions would include methylated forms of the amino acid sequence of the amino acid segment and methylated forms of the amino acid sequence of the amino acid segment include amino acid substitutions.

Protein variants and derivatives are well understood by those of skill in the art and can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof can be combined to arrive at a final construct. The mutations must not place the sequence out of reading frame and preferably will not create complementary regions that could produce secondary mRNA structure.

As used herein in reference to a specified amino acid sequence, a "conservative variant" is a sequence in which a first amino acid is replaced by another amino acid or amino acid analog having at least one biochemical property similar to that of the first amino acid; similar properties include, for example, similar size, charge, hydrophobicity or hydrogen-bonding capacity. Conservative variants are also referred to herein as "conservative amino acid substitutions," "conservative amino acid variants," "conservative substitutions," and similar phrase. A "conservative derivative" of a reference sequence refers to an amino acid sequence that differs from the reference sequences only in conservative substitutions.

As an example, a conservative variant can be a sequence in which a first uncharged polar amino acid is conservatively substituted with a second (non-identical) uncharged polar amino acid such as cysteine, serine, threonine, tyrosine, glycine, glutamine or asparagine or an analog thereof. A conservative variant also can be a sequence in which a first basic amino acid is conservatively substituted with a second basic amino acid such as arginine, lysine, histidine, 5-hydroxylysine, N-methyllysine or an analog thereof. Similarly, a conservative variant can be a sequence in which a first hydrophobic amino acid is conservatively substituted with a second hydrophobic amino acid such as alanine, valine, leucine, isoleucine, proline, methionine, phenylalanine or tryptophan or an analog thereof. In the same way, a conservative variant can be a sequence in which a first acidic amino acid is conservatively substituted with a second acidic amino acid such as aspartic acid or glutamic acid or an analog thereof; a sequence in which an aromatic amino acid such as phenylalanine is conservatively substituted with a second aromatic amino acid or amino acid analog, for example, tyrosine; or a sequence in which a first relatively small amino acid such as alanine is substituted with a second relatively small amino acid or amino acid analog such as glycine or valine or an analog thereof. For example, the replacement of one amino acid residue with another that is biologically and/or chemically similar is known to those skilled in the art as a conservative substitution. For example, a conservative substitution would be replacing one hydrophobic residue for another or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein. It is understood that conservative variants of the disclosed amino acid sequences can encompass sequences containing, for example, one, two, three, four or more amino acid substitutions relative to the reference sequence, and that such variants can include naturally and non-naturally occurring amino acid analogs.

Substitutional variants are those in which at least one residue has been removed and a different residue inserted in its place. Examples of such substitutions, referred to as conservative substitutions, can generally be made in accordance with the following Table 1.

TABLE 1

| Amino Acid Substitutions Original Residue Exemplary Conservative Substitutions, others are known in the art. | |
| --- | --- |
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity can be made by selecting substitutions that are less conservative, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation. These can be referred to as less conservative variants.

Peptides can have a variety of modifications. Modifications can be used to change or improve the properties of the peptides. For example, the disclosed peptides can be N-methylated, O-methylated, S-methylated, C-methylated, or a combination at one or more amino acids.

The amino and/or carboxy termini of the disclosed peptides can be modified. Amino terminus modifications include methylation (e.g., $-NHCH_3$ or $-N(CH_3)_2$), acetylation (e.g., with acetic acid or a halogenated derivative thereof such as α-chloroacetic acid, α-bromoacetic acid, or α-iodoacetic acid), adding a benzyloxycarbonyl (Cbz) group, or blocking the amino terminus with any blocking group containing a carboxylate functionality defined by RCOO— or sulfonyl functionality defined by $R-SO_2-$, where R is selected from the group consisting of alkyl, aryl, heteroaryl, alkyl aryl, and the like, and similar groups. One can also incorporate a desamino acid at the N-terminus (so that there is no N-terminal amino group) to decrease susceptibility to proteases or to restrict the conformation of the peptide compound. In preferred embodiments, the N-terminus is acetylated with acetic acid or acetic anhydride.

Carboxy terminus modifications include replacing the free acid with a carboxamide group or forming a cyclic lactam at the carboxy terminus to introduce structural constraints. One can also cyclize the disclosed peptides, or incorporate a desamino or descarboxy residue at the termini of the peptide, so that there is no terminal amino or carboxyl group, to decrease susceptibility to proteases or to restrict the conformation of the peptide. C-terminal functional groups of the disclosed peptides include amide, amide lower alkyl, amide di(lower alkyl), lower alkoxy, hydroxy, and carboxy, and the lower ester derivatives thereof, and the pharmaceutically acceptable salts thereof.

One can replace the naturally occurring side chains of the genetically encoded amino acids (or the stereoisomeric D amino acids) with other side chains, for instance with groups such as alkyl, lower ($C_{1-6}$) alkyl, cyclic 4-, 5-, 6-, to 7-membered alkyl, amide, amide lower alkyl amide di(lower alkyl), lower alkoxy, hydroxy, carboxy and the lower ester derivatives thereof, and with 4-, 5-, 6-, to 7-membered heterocyclic. In particular, proline analogues in which the ring size of the proline residue is changed from 5 members to 4, 6, or 7 members can be employed. Cyclic groups can be saturated or unsaturated, and if unsaturated, can be aromatic or non-aromatic. Heterocyclic groups preferably contain one or more nitrogen, oxygen, and/or sulfur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl. These heterocyclic groups can be substituted or unsubstituted. Where a group is substituted, the substituent can be alkyl, alkoxy, halogen, oxygen, or substituted or unsubstituted phenyl.

Peptides can also be modified with poly(ethylene glycol). A peptide containing poly(ethylene glycol) (also referred to as PEG) is also referred to as a "PEGylated" peptide. PEG coupled to peptides can be used for altering solubility characteristics in aqueous or organic solvents; for modulation of immune response; to increase the stability of peptides in solution; to enhance the half-life of peptides in vivo; to aid in penetrating cell membranes; to alter pharmacological properties; to increase biocompatibility, especially toward implanted foreign substances; and to reduce peptide adsorption to surfaces (Roberts, M., et al., Advanced Drug Delivery Reviews, 54:459-476 (2002)).

The polymer backbone of PEG is not of biological origin and therefore is not readily degraded by mammalian enzymes. This allows for slow degradation of the polymer when used in vivo which can extend the half-life of the PEGylated peptide.

PEG can be conjugated to peptides through its two hydroxyl groups at the ends of each linear chain. In some instances this process is done by the creation of a reactive electrophilic intermediate that is capable of spontaneously coupling to nucleophilic residues on a second molecule. Methods and techniques for PEGylating peptides are known in the art.

One can also readily modify peptides by phosphorylation, and other methods.

The disclosed peptides also serve as structural models for non-peptidic compounds with similar biological activity. Those of skill in the art recognize that a variety of techniques are available for constructing compounds with the same or similar desired biological activity as the lead peptide compound, but with more favorable activity than the lead with respect to solubility, stability, and susceptibility to hydrolysis and proteolysis. These techniques include, but are not limited to, replacing the peptide backbone with a backbone composed of phosphonates, amidates, carbamates, sulfonamides, secondary amines, and N-methylamino acids.

Molecules can be produced that resemble peptides, but which are not connected via a natural peptide linkage. For example, non-peptide linkages for amino acids or amino acid analogs can include $CH_2NH-$, $-CH_2S-$, $-CH_2-CH_2-$, $-CH=CH-$ (cis and trans), $-COCH_2-$, $-CH(OH)CH_2-$, and $-CHH_2SO-$. A particularly preferred non-peptide linkage is $-CH_2NH-$. It is understood that peptide analogs can have more than one atom between the bond atoms, such as β-alanine, γ-aminobutyric acid, and the like.

Substitutional or deletional mutagenesis can be employed to insert sites for N-glycosylation (Asn-X-Thr/Ser) or O-glycosylation (Ser or Thr). Deletions of cysteine or other labile residues also can be desirable. Deletions or substitutions of potential proteolysis sites, e.g. Arg, can be accomplished, for example, by deleting one of the basic residues or substituting one by glutaminyl or histidyl residues.

Certain post-translational derivatizations can be the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains, acetylation of the N-terminal amine and, in some instances, amidation of the C-terminal carboxyl.

2. Homology

One way to define the variants and derivatives of the disclosed amino acids sequences, amino acid segments, peptides, proteins, etc. is by defining the variants and derivatives in terms of homology/identity to specific known sequences. For example, specifically disclosed are variants of these and other amino acids sequences, amino acid segments, peptides, proteins disclosed which have at least, 70% or 75% or 80% or 85% or 90% or 95% homology or sequence identity to the stated sequence. Methods to determine the homology or sequence identity of two proteins are known in the art. For example, the homology can be calculated after aligning the two sequences so that the homology is at its highest level.

Another way of calculating homology or sequence identity can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

It is understood that the description of conservative variants and homology or sequence identity can be combined together in any combination, such as embodiments that have at least 70% homology or sequence identity to a particular sequence wherein the variants are conservative variants.

3. Multivalent Peptides

Also disclosed are bifunctional peptides, which contain the GM1-like peptide fused to a second peptide having a separate function. Such bifunctional peptides have at least two functions conferred by different portions of the full-length molecule and can, for example, display homing activity or antibacterial activity in addition to the ability to block binding of a ligand to GM1.

The disclosed peptides can be linked together to form divalent or multivalent peptides. In some embodiments, the peptides are directly linked together to form a polymer. Thus, disclosed is a peptide having two or more peptide sequences that compete for the binding of GM1 to anti-ganglioside antibodies or bacterial proteins. For example, disclosed is a peptide having two or more amino acid sequences set forth in SEQ ID NOs:1, 2, 3, 4, 5, or 6.

The disclosed multivalent peptides include at least two subsequences each independently containing a peptide or amino acid segment. The multivalent peptide can have, for example, at least three, at least five or at least ten of such subsequences each independently containing a peptide. In particular embodiments, the multivalent peptide can have two, three, four, five, six, seven, eight, nine, ten, fifteen or twenty identical or non-identical subsequences. This is in addition to the multiple GM1-like peptides that can comprise the disclosed compositions. In a further embodiment, the multivalent peptide can contain identical subsequences, such as repeats of a specified amino acid sequence. In a further embodiment, the multivalent peptide contains contiguous identical or non-identical subsequences, which are not separated by any intervening amino acids.

Two or more of the disclosed polypeptide can be linked together to form a conjugate. For example, disclosed is a composition including a first polypeptide having the amino acid sequence SEQ ID NO:1, 2, 3, 4, 5, or 6, or a conservative substitution or deletion thereof, and a second polypeptide having the amino acid sequence SEQ ID NO:1, 2, 3, 4, 5, or 6, or a conservative substitution or deletion thereof, wherein the first and second polypeptides are conjugated together with a linker. The linker can be any molecule, compound, or composition capable of joining two or more polypeptides together. For example, the linker can be one or more amino acids. The linker can be a polymer, such as polyethylene glycol (PEG).

Thus, in some embodiments, the polypeptides are linked to form a dendrimer. Peptide dendrimers are branched, often highly branched, artificial proteins in which several peptide chains branch out from a dendritic core matrix that is built up through the propagation of, for example, a trifunctional amino acid, such as Lys. Originally conceived as Multiple Antigen Presentation System (MAPs) for vaccine development, these molecules are also useful for protein design.

4. Peptidomimetic

A peptidomimetic can be substituted for any of the disclosed peptides. For example, a multivalent peptide can contain at least one peptidomimetic fused to either a peptide or to another peptidomimetic. A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; α,α.-dialkylglycine or α-aminocycloalkane carboxylic acid; an $N^{\alpha}$—$C^{\alpha}$ cyclized amino acid; an $N^{\alpha}$.-methylated amino acid; a β- or γ-amino cycloalkane carboxylic acid; an α,β-unsaturated amino acid; a β,β-dimethyl or β-methyl amino acid; a β-substituted-2,3-methano amino acid; an N—$C^{\epsilon}$ or $C^{\alpha}$—$C^{\Delta}$ cyclized amino acid; β-alanine, L-α-amino butyric acid, L-γ-amino butyric acid, L-α-amino isobutyric acid, L-ϵ-amino caproic acid, 7-amino heptanoic acid, L-aspartic acid, L-glutamic acid, N-ϵ-Boc-N-α-CBZ-L-lysine, N-ϵ-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioprolinea, substituted proline or another amino acid mimetic. A peptidomimetic which mimics peptide secondary structure can contain, for example, a non-peptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylene-sulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. As an example, the Cambridge Structural Database contains a collection of greater than 300,000 compounds that have known crystal structures (Allen et al., Acta Crystalloqr. Section B, 35:2331 (1979)). This structural depository is continually updated as new crystal structures are determined and can be screened for compounds having suitable shapes, for example, the same shape as a disclosed peptide, as well as potential geometrical and chemical complementarity to a ligand. Where no crystal structure of a peptide or a ligand that binds the peptide is available, a structure can be generated using, for example, the program CONCORD (Rusinko et al., J. Chem. Inf. Comput. Sci. 29:251 (1989)). Another database, the Available Chemicals Directory (Molecular Design Limited, Information Systems; San Leandro Calif.), contains about 100,000 compounds that are commercially available and also can be searched to identify potential peptidomimetics of a peptide, for example, with activity in selectively blocking interaction of GM1 with any ligand, for example anti-GM1 antibodies or bacterial proteins.

There are also numerous D amino acids or amino acids which have a different functional substituent than natural amino acids. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs). D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides.

5. Additional Moieties

The disclosed compositions can further include additional moieties, such as therapeutic agents or effector molecules. For example, the disclosed peptides, such as the GM1 ganglioside-like peptides, can further include an effector molecule. Examples of effector molecules include small molecules, pharmaceutical drugs, toxins, fatty acids, detectable agent, conjugating tags, nanoparticles, or enzymes. The effect of the effector molecule can, for example, be the labeling, activating, repressing, or killing of the target cell(s) or tissue.

The effector molecule can be a detectable agent which includes any substance that can be used to label or stain a target tissue or cell(s).

The effector molecule can be covalently linked to the disclosed peptide. The effector molecule can be linked to the amino terminal end of the disclosed peptide. The effector molecule can be linked to the carboxy terminal end of the disclosed peptide. The effector molecule can be linked to an amino acid within the disclosed peptide. The herein provided compositions can further include a linker connecting the effector molecule and disclosed peptide. The disclosed peptide can also be conjugated to a coating molecule such as bovine serum albumin (BSA) (see Tkachenko et al., (2003) J Am Chem Soc, 125, 4700-4701) that can be used to coat the Nanoshells with the peptide.

Protein crosslinkers that can be used to crosslink the effector molecule to the disclosed peptide are known in the art and are defined based on utility and structure. Representative linkers include DSS (Disuccinimidylsuberate), DSP (Dithiobis(succinimidylpropionate)), DTSSP (3,3'-Dithiobis(sulfosuccinimidylpropionate)), SULFO BSOCOES (Bis[2-(sulfosuccinimdooxycarbonyloxy)ethyl]sulfone), BSOCOES (Bis[2-(succinimdooxycarbonyloxy)ethyl]sulfone), SULFO DST (Disulfosuccinimdyltartrate), DST (Disuccinimdyltartrate), SULFO EGS (Ethylene glycolbis(succinimidylsuccinate)), EGS (Ethylene glycolbis(sulfosuccinimidylsuccinate)), DPDPB (1,2-Di[3'-(2'-pyridyldithio)propionamido]butane), BSSS (Bis(sulfosuccinimdyl)suberate), SMPB (Succinimdyl-4-(p-maleimidophenyl)butyrate), SULFO SMPB (Sulfosuccinimdyl-4-(p-maleimidophenyl)butyrate), MBS (3-Maleimidobenzoyl-N-hydroxysuccinimide ester), SULFO MBS (3-Maleimidobenzoyl-N-hydroxysulfosuccinimide ester), SIAB (N-Succinimidyl(4-iodoacetyl)aminobenzoate), SULFO SIAB (N-Sulfosuccinimidyl(4-iodoacetyl)aminobenzoate), SMCC (Succinimidyl-4-(N-maleimidomethyl)cyclohexane-1-carboxylate), SULFO SMCC (Sulfosuccinimidyl-4-(N-maleimidomethyl)cyclohexane-1-carboxylate), NHS LC SPDP (Succinimidyl-6-[3-(2-pyridyldithio)propionamido) hexanoate), SULFO NHS LC SPDP (Sulfosuccinimidyl-6-[3-(2-pyridyldithio)propionamido)hexanoate), SPDP (N-Succinimidyl-3-(2-pyridyldithio)propionate), NHS BROMOACETATE (N-Hydroxysuccinimidylbromoacetate), NHS IODOACETATE (N-Hydroxysuccinimidyliodoacetate), MPBH (4-(N-Maleimidophenyl)butyric acid hydrazide hydrochloride), MCCH (4-(N-Maleimidomethyl)cyclohexane-1-carboxylic acid hydrazide hydrochloride), MBH (m-Maleimidobenzoic acid hydrazidehydrochloride), SULFO EMCS(N-(epsilon-Maleimidocaproyloxy)sulfosuccinimide), EMCS(N-(epsilon-Maleimidocaproyloxy)succinimide), PMPI (N-(p-Maleimidophenyl)isocyanate), KMUH (N-(kappa-Maleimidoundecanoic acid) hydrazide), LC SMCC (Succinimidyl-4-(N-maleimidomethyl)-cyclohexane-1-carboxy(6-amidocaproate-)), SULFO GMBS (N-(gamma-Maleimidobutryloxy)sulfosuccinimide ester), SMPH (Succinimidyl-6-(beta-maleimidopropionamidohexanoate)), SULFO KMUS (N-(kappa-Maleimidoundecanoyloxy)sulfosuccinimide ester), GMBS (N-(gamma-Maleimidobutyrloxy)succinimide), DMP (Dimethylpimelimidate hydrochloride), DMS (Dimethylsuberimidate hydrochloride), MHBH (Wood's Reagent) (Methyl-p-hydroxybenzimidate hydrochloride, 98%), DMA (Dimethyladipimidate hydrochloride).

The effector molecule can be an agarose bead. For example, AminoLink® Coupling Resin can be used. This resin allows a peptide to be covalently linked to a beaded agarose support. The agarose bead support contains an aldehyde group that can react with the primary amine on a peptide or protein. The peptide-agarose bead conjugates can then be used for affinity purification of antibodies, other proteins or other biomolecules. These conjugates can be used multiple times and therefore are a cost-effective way to perform affinity purifications.

B. Nucleic Acids

1. Nucleic Acids Encoding the Peptides

Nucleic acids that can encode the disclosed peptide sequences are also provided. The nucleic acids, including degenerate nucleic acids, encode the disclosed variants and derivatives of the peptide sequences. While each particular nucleic acid sequence may not be written out, it is understood that each and every sequence is in fact disclosed and described through the disclosed protein sequence.

2. Expression Control Sequences

The nucleic acids that are delivered to cells typically contain expression control systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements. Thus, also disclosed are nucleic acids encoding the disclosed peptides operably linked to an expression control sequence.

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355-360 (1982)). Of course, promoters from the host cell or related species can also be used.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell. Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell Bio. 4: 1293 (1984)). They are usually between 10 and 300 by in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, .alpha.-fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and contains of about 400 bases. It is also preferred that the transcribed units contain other standard sequences alone or in combination with the above sequences improve expression from, or stability of, the construct.

3. Vectors Containing the Nucleic Acids

Also disclosed is a vector containing a nucleic acid encoding the disclosed peptides. In some embodiments the vector is derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens.

4. Cells Containing Vectors

Also disclosed are cells containing one or more of the disclosed nucleic acids or vectors. The term “cell” refers to individual cells, cell lines, primary culture, or cultures derived from such cells unless specifically indicated. A “culture” refers to a composition having isolated cells of the same or a different type. A cell line is a culture of a particular type of cell that can be reproduced indefinitely, thus making the cell line “immortal.” A cell culture can be a population of cells grown on a medium such as agar. A primary cell culture is a culture from a cell or taken directly from a living organism, which is not immortalized.

C. Pharmaceutical Compositions

The disclosed compositions can be administered in vivo either alone or in a pharmaceutically acceptable carrier. By “pharmaceutically acceptable” is meant a material that is not biologically or otherwise undesirable, i.e., the material can be administered to a subject, along with the composition disclosed herein, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. The materials can be in solution, suspension (for example, incorporated into micro-particles, liposomes, or cells).

1. Pharmaceutically Acceptable Carriers

The compositions disclosed herein can be used prophylactically and therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers can be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

a. Liposomes

Pharmaceutical composition having an effective amount of one or more peptides can be carried in a liposome. Liposomes can be used to package any biologically active agent for delivery to cells.

Materials and procedures for forming liposomes are well-known to those skilled in the art. Upon dispersion in an appropriate medium, a wide variety of phospholipids swell, hydrate and form multilamellar concentric bilayer vesicles with layers of aqueous media separating the lipid bilayers. These systems are referred to as multilamellar liposomes or multilamellar lipid vesicles ("MLVs") and have diameters within the range of 10 nm to 100 .mu.m. These MLVs were first described by Bangham, et al., J. Mol. Biol. 13:238-252 (1965). In general, lipids or lipophilic substances are dissolved in an organic solvent. When the solvent is removed, such as under vacuum by rotary evaporation, the lipid residue forms a film on the wall of the container. An aqueous solution that typically contains electrolytes or hydrophilic biologically active materials is then added to the film. Large MLVs are produced upon agitation. When smaller MLVs are desired, the larger vesicles are subjected to sonication, sequential filtration through filters with decreasing pore size or reduced by other forms of mechanical shearing. There are also techniques by which MLVs can be reduced both in size and in number of lamellae, for example, by pressurized extrusion (Barenholz, et al., FEBS Lett. 99:210-214 (1979)).

Liposomes can also take the form of unilamnellar vesicles, which are prepared by more extensive sonication of MLVs, and are made of a single spherical lipid bilayer surrounding an aqueous solution. Unilamellar vesicles ("ULVs") can be small, having diameters within the range of 20 to 200 nm, while larger ULVs can have diameters within the range of 200 nm to 2 .mu.m. There are several well-known techniques for making unilamellar vesicles. In Papahadjopoulos, et al., Biochim et Biophys Acta 135:624-238 (1968), sonication of an aqueous dispersion of phospholipids produces small ULVs having a lipid bilayer surrounding an aqueous solution. Schneider, U.S. Pat. No. 4,089,801 describes the formation of liposome precursors by ultrasonication, followed by the addition of an aqueous medium containing amphiphilic compounds and centrifugation to form a biomolecular lipid layer system.

Small ULVs can also be prepared by the ethanol injection technique described by Batzri, et al., Biochim et Biophys Acta 298:1015-1019 (1973) and the ether injection technique of Deamer, et al., Biochim et Biophys Acta 443:629-634 (1976). These methods involve the rapid injection of an organic solution of lipids into a buffer solution, which results in the rapid formation of unilamellar liposomes. Another technique for making ULVs is taught by Weder, et al. in "Liposome Technology", ed. G. Gregoriadis, CRC Press Inc., Boca Raton, Fla., Vol. I, Chapter 7, pg. 79-107 (1984). This detergent removal method involves solubilizing the lipids and additives with detergents by agitation or sonication to produce the desired vesicles.

Papahadjopoulos, et al., U.S. Pat. No. 4,235,871, describes the preparation of large ULVs by a reverse phase evaporation technique that involves the formation of a water-in-oil emulsion of lipids in an organic solvent and the drug to be encapsulated in an aqueous buffer solution. The organic solvent is removed under pressure to yield a mixture which, upon agitation or dispersion in an aqueous media, is converted to large ULVs. Suzuki et al., U.S. Pat. No. 4,016,100, describes another method of encapsulating agents in unilamellar vesicles by freezing/thawing an aqueous phospholipid dispersion of the agent and lipids.

In addition to the MLVs and ULVs, liposomes can also be multivesicular. Described in Kim, et al., Biochim et Biophys Acta 728:339-348 (1983), these multivesicular liposomes are spherical and contain internal granular structures. The outer membrane is a lipid bilayer and the internal region contains small compartments separated by bilayer septum. Still yet another type of liposomes are oligolamellar vesicles ("OLVs"), which have a large center compartment surrounded by several peripheral lipid layers. These vesicles, having a diameter of 2-15 .mu.m, are described in Callo, et al., Cryobiology 22(3):251-267 (1985).

Mezei, et al., U.S. Pat. Nos. 4,485,054 and 4,761,288 also describe methods of preparing lipid vesicles. More recently, Hsu, U.S. Pat. No. 5,653,996 describes a method of preparing liposomes utilizing aerosolization and Yiournas, et al., U.S. Pat. No. 5,013,497 describes a method for preparing liposomes utilizing a high velocity-shear mixing chamber. Methods are also described that use specific starting materials to produce ULVs (Wallach, et al., U.S. Pat. No. 4,853,228) or OLVs (Wallach, U.S. Pat. Nos. 5,474,848 and 5,628,936).

A comprehensive review of all the aforementioned lipid vesicles and methods for their preparation are described in "Liposome Technology", ed. G. Gregoriadis, CRC Press Inc., Boca Raton, Fla., Vol. I, II & III (1984). This and the aforementioned references describing various lipid vesicles suitable for use in the invention are incorporated herein by reference.

Fatty acids (i.e., lipids) that can be conjugated to the provided compositions include those that allow the efficient incorporation of the disclosed compositions into liposomes. Generally, the fatty acid is a polar lipid. Thus, the fatty acid can be a phospholipid. The provided compositions can include either natural or synthetic phospholipid. The phospholipids can be selected from phospholipids containing saturated or unsaturated mono or disubstituted fatty acids and combinations thereof. These phospholipids can be dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palmitoyloleoylphosphatidylserine, palmitoyloleoylphosphatidylethanolamine, palmitoyloleoylphophatidylglycerol, palmitoyloleoylphosphatidic acid, palmitelaidoyloleoylphosphatidylcholine, palmitelaidoyloleoylphosphatidylserine, palmitelaidoyloleoylphosphatidylethanolamine, palmitelaidoyloleoylphosphatidylglycerol, palmitelaidoyloleoylphosphatidic acid, myristoleoyloleoylphosphatidylcholine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidylglycerol, dilinoleoylphosphatidic acid, palmitielinoleoylphosphatidylcholine, palmiticlinoleoylphosphatidylserine, palmiticlinoleoylphosphatidylethanolamine, palmiticlinoleoylphosphatidylglycerol, palmiticlinoleoylphosphatidic acid. These phospholipids may also be the monoacylated derivatives of phosphatidylcholine (lysophophatidylidylcholine), phosphatidylserine (lysophosphatidylserine), phosphatidylethanolamine(lysophosphatidylethanolamine), phophatidylglycerol (lysophosphatidylglycerol) and phosphatidic acid (lysophosphatidic acid). The monoacyl chain in these lysophosphatidyl derivatives may be palimtoyl, oleoyl, palmitoleoyl, linoleoyl myristoyl or myristoleoyl. The phospholipids can also be synthetic. Synthetic phospholipids are readily available commercially from various sources, such as AVANTI Polar Lipids (Albaster, Ala.); Sigma Chemical Company (St. Louis, Mo.). These synthetic compounds may be varied and may have variations in their fatty acid side chains not found in naturally occurring phospholipids. The fatty acid can have unsaturated fatty acid side chains with C14, C16, C18 or C20 chains length in either or both the PS or PC. Synthetic phospholipids can have dioleoyl (18:1)-PS; palmitoyl (16:0)-oleoyl (18:1)-PS, dimyristoyl (14:0)-PS; dipalmitoleoyl (16:1)-PC, dipalmitoyl (16:0)-PC, dioleoyl (18:1)-PC, palmitoyl (16:0)-oleoyl (18:1)-PC, and myristoyl (14:0)-oleoyl (18:1)-PC as constituents. Thus, as an example, the provided compositions can include palmitoyl 16:0.

C. Therapeutic and Detectable Agents

1. Therapeutic Agent

The compositions can comprise a therapeutic agent in addition to the disclosed peptides or peptidomimetics. As used herein, the term "therapeutic agent" means a molecule which can have one or more biological activities in a normal or pathologic tissue. A variety of therapeutic agents can be used. For example, the therapeutic agent can comprise a compound or composition for treating inflammation. The therapeutic agent can comprise a compound or composition to induce programmed cell death or apoptosis.

A therapeutic agent can be a therapeutic polypeptide. As used herein, a therapeutic polypeptide can be any polypeptide with a biologically useful function to treat the subject. Useful therapeutic polypeptides encompass, without limitation, cytokines, antibodies, cytotoxic polypeptides; pro-apoptotic polypeptides; and anti-angiogenic polypeptides. As non-limiting examples, useful therapeutic polypeptides can be a cytokine such as tumor necrosis factor-$\alpha$ (TNF-$\alpha$), tumor necrosis factor-$\beta$ (TNF-$\beta$), granulocyte macrophage colony stimulating factor (GM-CSF), granulocyte colony stimulating factor (G-CSF), interferon-$\alpha$ (IFN-$\alpha$); interferon-$\gamma$ (IFN-$\gamma$), interleukin-1 (IL-1), interleukin-2 (IL-2), interleukin-3 (IL-3), interleukin-4 (IL-4), interleukin-6 (IL-6), interleukin-7 (IL-7), interleukin-10 (IL-10), interleukin-12 (IL-12), lymphotactin (LTN) or dendritic cell chemokine 1 (DC-CK1); an anti-HER2 antibody or fragment thereof; a cytotoxic polypeptide including a toxin or caspase. It is understood that these and other polypeptides with biological activity can be a "therapeutic polypeptide."

The therapeutic agent can include one or more of classes of antibiotics known in the art.

Antimicrobial peptides can also be used. Thus, for example, also disclosed are therapeutic agents comprising an antimicrobial peptide, where the composition is selectively internalized and exhibits a high toxicity to the targeted area. Useful antimicrobial peptides can have low mammalian cell toxicity when not incorporated into the composition. As used herein, the term "antimicrobial peptide" means a naturally occurring or synthetic peptide having antimicrobial activity, which is the ability to kill or slow the growth of one or more microbes. An antimicrobial peptide can, for example, kill or slow the growth of one or more strains of bacteria including a Gram-positive or Gram-negative bacteria, or a fungi or protozoa. Thus, an antimicrobial peptide can have, for example, bacteriostatic or bacteriocidal activity against, for example, one or more strains of *Escherichia coli, Pseudomonas aeruginosa* or *Staphylococcus aureus*. While not wishing to be bound by the following, an antimicrobial peptide can have biological activity due to the ability to form ion channels through membrane bilayers as a consequence of self-aggregation.

An antimicrobial peptide is typically highly basic and can have a linear or cyclic structure. As discussed further below, an antimicrobial peptide can have an amphipathic α-helical structure (see U.S. Pat. No. 5,789,542; Javadpour et al., J. Med. Chem. 39:3107-3113 (1996); and Blondelle and Houghten, Biochem. 31: 12688-12694 (1992)). An antimicrobial peptide also can be, for example, a β-strand/sheet-forming peptide as described in Mancheno et al., J. Peptide Res. 51:142-148 (1998).

An antimicrobial peptide can be a naturally occurring or synthetic peptide. Naturally occurring antimicrobial peptides have been isolated from biological sources such as bacteria, insects, amphibians, and mammals and are thought to represent inducible defense proteins that can protect the host organism from bacterial infection. Naturally occurring antimicrobial peptides include the gramicidins, magainins, mellitins, defensins and cecropins (see, for example, Maloy and Kari, Biopolymers 37:105-122 (1995); Alvarez-Bravo et al., Biochem. J. 302:535-538 (1994); Bessalle et al., FEBS 274:-151-155 (1990.); and Blondelle and Houghten in Bristol (Ed.), Annual Reports in Medicinal Chemistry pages 159-168 Academic Press, San Diego). An antimicrobial peptide also can be an analog of a natural peptide, especially one that retains or enhances amphipathicity.

An antimicrobial peptide incorporated into the composition disclosed herein can have low mammalian cell toxicity when linked to the composition. Mammalian cell toxicity readily can be assessed using routine assays. As an example, mammalian cell toxicity can be assayed by lysis of human erythrocytes in vitro as described in Javadpour et al., supra, 1996. An antimicrobial peptide having low mammalian cell toxicity is not lytic to human erythrocytes or requires concentrations of greater than 100 μM for lytic activity, preferably concentrations greater than 200, 300, 500 or 1000 μM.

In one embodiment, disclosed are compositions in which the antimicrobial peptide portion promotes disruption of mitochondrial membranes when internalized by eukaryotic cells. In particular, such an antimicrobial peptide preferentially disrupts mitochondrial membranes as compared to eukaryotic membranes. Mitochondrial membranes, like bacterial membranes but in contrast to eukaryotic plasma membranes, have a high content of negatively charged phospholipids. An antimicrobial peptide can be assayed for activity in disrupting mitochondrial membranes using, for example, an assay for mitochondrial swelling or another assay well known in the art.

An antimicrobial peptide that induces significant mitochondrial swelling at, for example, 50 μM, 40 μM, 30 μM, 20 μM, 10 μM or less, is considered a peptide that promotes disruption of mitochondrial membranes.

Antimicrobial peptides generally have random coil conformations in dilute aqueous solutions, yet high levels of helicity can be induced by helix-promoting solvents and amphipathic media such as micelles, synthetic bilayers or cell membranes. α-Helical structures are well known in the art, with an ideal α-helix characterized by having 3.6 residues per turn and a translation of 1.5 Å per residue (5.4 Å per turn; see Creighton, Proteins: Structures and Molecular Properties W. H Freeman, New York (1984)). In an amphipathic α-helical structure, polar and non-polar amino acid residues are aligned into an amphipathic helix, which is an α-helix in which the hydrophobic amino acid residues are predominantly on one face, with hydrophilic residues predominantly on the opposite face when the peptide is viewed along the helical axis.

Antimicrobial peptides of widely varying sequence have been isolated, sharing an amphipathic α-helical structure as a common feature (Saberwal et al., Biochim. Biophys. Acta 1197:109-131 (1994)). Analogs of native peptides with amino acid substitutions predicted to enhance amphipathicity and helicity typically have increased antimicrobial activity. In general, analogs with increased antimicrobial activity also have increased cytotoxicity against mammalian cells (Maloy et al., Biopolymers 37:105-122 (1995)).

As used herein in reference to an antimicrobial peptide, the term "amphipathic α-helical structure" means an α-helix with a hydrophilic face containing several polar residues at physiological pH and a hydrophobic face containing nonpolar residues. A polar residue can be, for example, a lysine or arginine residue, while a nonpolar residue can be, for example, a leucine or alanine residue. An antimicrobial peptide having an amphipathic .alpha.-helical structure generally has an equivalent number of polar and nonpolar residues within the amphipathic domain and a sufficient number of basic residues to give the peptide an overall positive charge at neutral pH (Saberwal et al., Biochim. Biophys. Acta 1197: 109-131 (1994)). One skilled in the art understands that helix-promoting amino acids such as leucine and alanine can be advantageously included in an antimicrobial peptide (see, for example, Creighton, supra, 1984). Synthetic, antimicrobial peptides having an amphipathic α-helical structure are known in the art, for example, as described in U.S. Pat. No. 5,789,542 to McLaughlin and Becker.

2. Detectable Agent

The moiety in the disclosed compositions can also be a detectable agent. A variety of detectable agents are useful in the disclosed methods. As used herein, the term "detectable agent" refers to any molecule which can be detected. Useful detectable agents include compounds and molecules that can be administered in vivo and subsequently detected. Detectable agents useful in the disclosed compositions and methods include yet are not limited to radiolabels and fluorescent molecules. The detectable agent can be, for example, any molecule that facilitates detection, either directly or indirectly, preferably by a non-invasive and/or in vivo visualization technique. For example, a detectable agent can be detectable by any known imaging techniques, including, for example, a radiological technique, a magnetic resonance technique, or an ultrasound technique. Detectable agents can include, for example, a contrasting agent, e.g., where the contrasting agent is ionic or non-ionic. In some embodiments, for instance, the detectable agent comprises a tantalum compound and/or a barium compound, e.g., barium sulfate. In some embodiments, the detectable agent comprises iodine, such as radioactive iodine. In some embodiments, for instance, the detectable agent comprises an organic iodo acid, such as iodo carboxylic acid, triiodophenol, iodoform, and/or tetraiodoethylene. In some embodiments, the detectable agent comprises a non-radioactive detectable agent, e.g., a non-radioactive isotope. For example, Gd can be used as a non-radioactive detectable agent in certain embodiments.

Other examples of detectable agents include molecules which emit or can be caused to emit detectable radiation (e.g., fluorescence excitation, radioactive decay, spin resonance excitation, etc.), molecules which affect local electromagnetic fields (e.g., magnetic, ferromagnetic, ferromagnetic, paramagnetic, and/or superparamagnetic species), molecules which absorb or scatter radiation energy (e.g., chromophores and/or fluorophores), quantum dots, heavy elements and/or compounds thereof. See, e.g., detectable agents described in U.S. Pat. No. 7,413,727. Other examples of detectable agents include a proton-emitting molecules, a radiopaque molecules, and/or a radioactive molecules, such as a radionuclide like Tc-99m and/or Xe-13. Such molecules can be used as a radiopharmaceutical. In still other embodiments, the disclosed compositions can comprise one or more different types of detectable agents, including any combination of the detectable agents disclosed herein.

Useful fluorescent moieties are well known in the art. In some embodiments, compositions comprising a radioactive detectable agent can be prepared by coupling a targeting moiety with radioisotopes suitable for detection. Coupling can occur via a chelating agent such as diethylenetriaminepentaacetic acid (DTPA), 4,7,10-tetraazacyclododecane-N-, N',N",N'"-tetraacetic acid (DOTA) and/or metallothionein, any of which can be covalently attached to the targeting moiety. In some embodiments, an aqueous mixture of technetium-99m, a reducing agent, and a water-soluble ligand can be prepared and then allowed to react with a disclosed targeting moiety. Such methods are known in the art, see e.g., International Publication No. WO 99/64446. In some embodiments, compositions comprising radioactive iodine, can be prepared using an exchange reaction. For example, exchange of hot iodine for cold iodine is well known in the art. Alternatively, a radio-iodine labeled compound can be prepared from the corresponding bromo compound via a tributylstannyl intermediate.

Magnetic detectable agents include paramagnetic contrasting agents, e.g., gadolinium diethylenetriaminepentaacetic acid, e.g., used with magnetic resonance imaging (MRI) (see, e.g., De Roos, A. et al., Int. J. Card. Imaging Vol. 7 pg. 133 (1991)). Some preferred embodiments use as the detectable agent paramagnetic atoms that are divalent or trivalent ions of elements with an atomic number 21, 22, 23, 24, 25, 26, 27, 28, 29, 42, 44, 58, 59, 60, 61, 62, 63, 64, 65, 66, 67, 68, 69, or 70.

In some embodiments, compositions comprising magnetic detectable agents can be prepared by coupling a targeting moiety with a paramagnetic atom. For example, the metal oxide or a metal salt, such as a nitrate, chloride or sulfate salt, of a suitable paramagnetic atom can be dissolved or suspended in a water/alcohol medium, such as methyl, ethyl, and/or isopropyl alcohol. The mixture can be added to a solution of an equimolar amount of the targeting moiety in a similar water/alcohol medium and stirred. The mixture can be heated moderately until the reaction is complete or nearly complete. Insoluble compositions formed can be obtained by filtering, while soluble compositions can be obtained by evaporating the solvent. If acid groups on the chelating moieties remain in the disclosed compositions, inorganic bases (e.g., hydroxides, carbonates and/or bicarbonates of sodium, potassium and/or lithium), organic bases, and/or basic amino acids can be used to neutralize acidic groups, e.g., to facilitate isolation or purification of the composition.

The detectable agent can be coupled to the composition in such a way so as not to interfere with the ability of the peptide to interact with the target site. In some embodiments, the detectable agent can be chemically bound to the peptide. In some embodiments, the detectable agent can be chemically bound to a therapeutic agent that is itself chemically bound to the peptide, indirectly linking the detectable agent and GM1-like peptide.

III. METHODS

A. Method of Treating Ganglioside-Associated Disorders or Infections

Ganglioside-associated disorders or infections, such as GM1-associated disorders or infections, can be treated by interfering with the role of the ganglioside in the disorder or infection. For example, GM1 can be targeted by certain bacterial proteins, such as cholera toxin B subunit (CTB). The interaction of CTB with GM1 allows for penetration of the bacteria into the cell. The ganglioside disorder or infection can be treated by interfering with the CTB:GM1 interaction. This results in the bacteria being unable to enter cells.

The methods of treating can involve administering an effective amount of a pharmaceutical composition to inhibit binding of a disease agent or infectious agent to GM1. The pharmaceutical composition can include a GM1-like peptide.

1. Disorders or Infections

Gangliosides are involved in the pathology of several diseases, disorders and infections. Gangliosides are glycosphingolipids often found on cell surfaces. Gangliosides contain three elements: (1) one or more sialic acid residues attached to (2) an oligosaccharide or carbohydrate core moiety, which in turn is attached to (3) a hydrophobic lipid (ceramide) structure which generally is embedded in the cell membrane. The ceramide moiety includes a long chain base portion and a fatty acid portion. Gangliosides, as well as other glycolipids and their structures in general, are discussed in, for example, Lehninger, Biochemistry (Worth Publishers, 1981) pp. 287-295 and Devlin, Textbook of Biochemistry (Wiley-Liss, 1992). Gangliosides are classified according to the number of monosaccharides in the carbohydrate moiety, as well as the number and location of sialic acid groups present in the carbohydrate moiety. Mono sialogangliosides are given the designation "GM". Further classification is based on the number of saccharides present in the oligosaccharide core. For example, a GM1 ganglioside has five saccharide residues [Gal-GalNAc-(NeuAc)-Gal-Glc-].

Gangliosides are normal components of plasma membranes and are particularly abundant in the nervous system. In humans, gangliosides are most abundant in the gray matter of the brain, particularly in nerve endings. They are believed to be present at receptor sites for neurotransmitters, including acetylcholine, and can also act as specific receptors for other biological macromolecules, including interferon, hormones, viruses, bacterial toxins, and the like.

GM1 ganglioside is involved in the pathology of disorders and infections, such as Guillain-Barré Syndrome (GBS), *Vibrio cholerae* and Enterotoxigenic *E. coli* (ETEC). In GBS, autoantibodies to GM1 are present and contribute to the disease pathology. For cholera and ETEC, cholera toxin B subunit and ETEC B subunit bind GM1 to facilitate the penetration of the bacteria into cells.

a. GBS

GBS is an autoimmune, acute, inflammatory, demyelinating polyneuropathy with a variant form designated as acute motor axonal neuropathy. Anti-ganglioside antibodies contribute to the pathogenesis. Gangliosides are abundantly expressed in human nerves and have important roles as mediators of cell adhesion and modulators of signal transduction. Molecular mimicry between microbial lipooligosaccharide antigens and endogenous ganglioside GM1 has been proposed as an etiological mechanism for GBS. Autoantibodies for GM1 [Galβ1-3GalNacβ1-4(NeuAcα2-3)Galβ1-4Glcβ1-1'Cer-] can often be elicited by preceding infections by *Campylobacter jejuni*. Moreover, elevated titers of circulating antibodies to GD3 ganglioside [NeuAcα2-8NeuAcα2-3Galβ1-4Glcβ1-1'Cer] occur in some patients with inflammatory demyelinating polyneuropathies.

b. Cholera

*Vibrio cholerae* is a major bacterial infectious agent of the small intestine. Due in part to its extremely short incubation period (two hours to five days), devastating cholera outbreaks can arise very quickly. Cholera is a potentially life threatening disease endemic to many parts of the world. The infection is most prevalent in developing countries that have poor sanitary conditions, causing many deaths worldwide. For cholera alone, it has been estimated that it affects 3-5 million people and causing over 100,000-130,000 deaths (WHO 2010). The major symptoms of the affected patients include profuse watery diarrhea and vomiting, which could lead to rapid dehydration, electrolyte imbalance and kidney failure, leading to death.

The bacterium contains cholera toxin (CT). CT is the causative agent for developing the clinical symptoms. CT consists of one A subunit and 5 identical B subunits as heterohexamers. The A subunit is responsible for ADP-ribosylation of the G-protein in the luminal side of the epithelial cells in the host guts. The B subunit, on the other hand, facilitates the penetration of the A subunit into the cell. Each of the B subunits binds to one suitable receptor on the cell surface. The receptor has been identified as ganglioside GM1. Thus, blocking the attachment of CTB to its cell surface receptor, such as GM1 or other GM1 analogues, is expected to prevent infection and the development of clinical symptoms.

c. ETEC

Enterotoxigenic *Escherichia coli* (ETEC) is the leading cause of diarrhea in the developing world and is commonly known as Traveler's diarrhea. It affects several hundred million people world wide and can often be fatal in developing countries. The bacterium contains a heat-labile enterotoxin. The heat-labile enterotoxin is similar structurally, functionally and immunologically to CT from *V. cholerae*. It is the causative agent for developing the clinical symptoms. ETEC consists of one A subunit and 5 identical B subunits as heterohexamers. The A subunit is responsible for ADP-ribosylation of the G-protein in the luminal side of the epithelial cells in the host guts. The B subunit, on the other hand, facilitates the penetration of the A subunit into the cell. Each of the B subunits binds to one suitable receptor on the cell surface. The receptor has been identified as ganglioside GM1. Thus, blocking the attachment of ETEC to its cell surface receptor, such as GM1 or other GM1 analogues, is expected to prevent infection and the development of clinical symptoms.

2. Combination Therapies

In some embodiments, the disclosed methods further involve administering to the subject a therapeutic agent. For example, the provided composition(s) can further comprise any of the therapeutic agents known in the art. The therapeutic agent can be but is not limited to immunotherapy, antimicrobials or anti-inflammatory agents as described above. One of the disclosed peptides in combination with a therapeutic agent, such as an antibiotic, can be used in the disclosed methods.

B. Methods of Inhibiting or Interfering with Binding of a Ganglioside with its Ligand The methods disclosed herein allow for the blocking, inhibition, or interference of the interaction between a ganglioside, such as GM1, and one of its ligands. For example, GM1-like peptides can be used to bind cholera toxin B subunit which would prevent the cholera toxin from being able to interact or bind with GM1. GM1-like peptides can also be used to bind antibodies that bind GM1, such as autoantibodies to GM1 found in GBS. Neutralizing the GM1 autoantibodies blocks the antibodies from binding GM1. Neutralization of autoantibodies can reduce disease symptoms or pathology.

C. Methods of Detecting Molecules Bound to GM1-Like Peptides

The disclosed compositions can be used in methods of detection. For example, the compositions can comprise a GM1-like peptide linked or conjugated to a detectable agent. The GM1-like peptide can bind to its ligand (i.e. cholera toxin or anti-GM1 antibodies) and the detectable agent can be used to detect or identify the conjugate. The presence of the conjugate indicates the presence of cholera toxin or anti-GM1 antibodies.

The methods of detecting can be performed in vivo or in vitro.

D. Administration and Delivery of Compositions

The disclosed compositions can be administered in any suitable manner. The manner of administration can be chosen based on, for example, whether local or systemic treatment is desired, on the area to be treated, and on what type of composition is being delivered (e.g., peptide, nucleic acid, etc.). For example, the compositions can be administered orally, parenterally (e.g., intravenous, subcutaneous, intraperitoneal, or intramuscular injection), by inhalation, extracorporeally, topically (including transdermally, ophthalmically, vaginally, rectally, intranasally) or the like.

For oral administration, solid dosage forms of tablets, capsules, pills, and granules can be prepared with coatings and shells such as enteric coatings and other coatings well-known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. The peptides can also be in micro-encapsulated form, if appropriate, with one or more excipients.

Peptides may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. For example, PEGylation is a preferred chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane.

For oral formulations, the location of release may be the stomach, the small intestine (the duodenum, the jejunem, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the peptide (or derivative) or by release of the peptide (or derivative) beyond the stomach environment, such as in the intestine.

To ensure full gastric resistance a coating can be impermeable to at least pH 5.0. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (i.e. powder), for liquid forms a soft gelatin shell may be used. The shell material of cachets could be thick starch or other edible paper. For pills, lozenges, molded tablets or tablet triturates, moist massing techniques can be used.

To aid dissolution of peptides into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 20, 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of peptides are for instance the fatty acids oleic acid, linoleic acid and linolenic acid.

Controlled release oral formulations may be desirable. The peptides could be incorporated into an inert matrix which permits release by either diffusion or leaching mechanisms, e.g., gums. Slowly degenerating matrices may also be incorporated into the formulation. Some enteric coatings also have a delayed release effect. Another form of a controlled release is by a method based on the Oros therapeutic system (Alza Corp.), i.e. the drug is enclosed in a semipermeable membrane which allows water to enter and push drug out through a single small opening due to osmotic effects.

Other coatings may be used for the formulation. These include a variety of sugars which could be applied in a coating pan. The peptides could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

Parenteral administration of the composition is generally characterized by injection. Injectables can be prepared in conventional forms, either as liquid solutions or suspensions, solid forms suitable for solution of suspension in liquid prior to injection, or as emulsions. Parenteral administration can involve the use of a slow release or sustained release system such that a constant dosage is maintained.

The compositions can also be administered intranasally. As used herein, "topical intranasal administration" means delivery of the compositions into the nose and nasal passages through one or both of the nares and can involve delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation.

The exact amount of the compositions required can vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. Thus, effective dosages and schedules for administering the compositions may be determined empirically, and making such determinations is within the skill in the art.

Dosage regimens are adjusted to provide the optimum desired response (e.g., effective amount or a therapeutic amount). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Generally, the dosage can vary with the age, condition, sex and extent of the disease in the patient, route of administration, or whether other drugs are included in the regimen, and can be determined by one of skill in the art. The dosage can be adjusted by the individual physician in the event of any counter indications. Guidance can be found in the literature for appropriate dosages for given classes of pharmaceutical products.

For example, a typical daily dosage of a composition having a peptide used alone might range from about 1 μg/kg to up to 100 mg/kg of body weight or more per day, depending on the factors mentioned above. For example dosages can be about 0.01 to 5 mg/kg of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg body weight.

Dosage can vary, and can be administered in one or more dose administrations daily, for one or several days. An exemplary treatment regime entails administration twice per day, once per day, once per week, once every two weeks, once every three weeks, once every four weeks, once a month, once every 3 months or once every three to 6 months.

The compositions disclosed herein can be administered prophylactically to patients or subjects who are at risk for bacterial infection, such as cholera toxin or *E. coli*, or diseases, such as GBS, or therapeutically to patients who have been newly diagnosed with a bacterial infection or GBS.

E. Methods of Making the Compositions

The compositions disclosed herein and the compositions necessary to perform the disclosed methods can be made using conventional techniques known to those of skill in the art for that particular reagent or compound unless otherwise specifically noted.

1. Peptide Synthesis

One method of producing the disclosed proteins is to link two or more peptides together by protein chemistry techniques. For example, peptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides can be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

2. Nucleic Acid Synthesis

Likewise, the nucleic acids can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method). Protein nucleic acid molecules can be made using known methods such as those described by Nielsen et al., Bioconjug. Chem. 5:3-7 (1994).

F. Methods of Screening

1. Identifying Ganglioside-Epitopes

Also provided is a method of identifying an agent that can be used to treat disorders, such as GBS, and infections, such as Cholera. In some embodiments, the method involves identifying molecules, such as peptides, having a ganglioside epitope, such as a GM1 epitope.

The method can involve providing a sample having a ganglioside binding molecule, such as CTB, under conditions that allow the binding of CTB to the ganglioside or a fragment thereof, and then detecting the level of CTB/ganglioside binding and comparing the binding level to a control. A decrease in CTB/ganglioside binding compared to the control indicates a molecule that can be used to treat GBS or Cholera.

The method can alternatively involve providing a sample containing a ganglioside binding molecule, such as CTB, under physiological conditions, and contacting the sample with a candidate molecule, and detecting the ability of the CTB to specifically bind to the candidate molecule, wherein the ability of the CTB to specifically bind the candidate molecule is an indication that the molecule can be used to treat disorders or infections, such as GBS and cholera.

The binding of the CTB to the ganglioside or the candidate molecule can be detected using routine methods, such as immunodetection methods, that do not disturb protein binding. For example, a CTB antibody can be used to detect the CTB bound to the ganglioside. The methods can be cell-based or cell-free assays. The steps of various useful immunodetection methods have been described in the scientific literature, such as, e.g., Maggio et al., Enzyme-Immunoassay, (1987) and Nakamura, et al., Enzyme Immunoassays: Heterogeneous and Homogeneous Systems, Handbook of Experimental Immunology, Vol. 1: Immunochemistry, 27.1-27.20 (1986), each of which is incorporated herein by reference in its entirety and specifically for its teaching regarding immunodetection methods. Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

EXAMPLES

Example I

GM1-Like Peptides

GM1-like peptides and their analogues have been developed using a dodecamer phage-displayed random library by screening with cholera toxin B subunit (CTB). Six peptides were selected by biopanning and recognition with CTB. The sequence information is shown in Table 2. Their degree of mimicry was confirmed with GM1.

TABLE 2

GM1-like peptides

| Peptides | | Amino Acid Sequence |
|---|---|---|
| $P_{GM1}$-1 | CT4-1, 3 | VSWKT**WFP**NLAV (SEQ ID NO: 1) |
| $P_{GM1}$-2 | CT4-4, 21, 24, 26, 28, 32 | YSP**F**HK**WFP**SMH (SEQ ID NO: 2) |
| $P_{GM1}$-3 | CT4-8 | IPQVWRDWFKLP (SEQ ID NO: 3) |
| $P_{GM1}$-4 | CT4-27 | **FPAWF**TKLYPRT (SEQ ID NO: 4) |

TABLE 2-continued

GM1-like peptides

| Peptides | | Amino Acid Sequence |
|---|---|---|
| $P_{GM1}$-5 | CT4-18 | QINTAKWWKTH**F** (SEQ ID NO: 5) |
| $P_{GM1}$-6 | CT4-29 | DASKALRSSGMP (SEQ ID NO: 6) |

*Phage displayed consensus amino acids are shown in boldface.

The inhibitory activities of these peptides were tested against CTB and rabbit anti-GM1 antibodies using a solid-phase ELISA. Since binding of CTB is not limited to GM1 but also to several other ligands, the relative inhibitory activities of these peptides for binding of fucosyl-GM1, GD1b, and $LOS_{GM1}$ with CTB was tested. The results are shown in Tables 3.

TABLE 3

Inhibitory activity of peptides on CTB binding by use of various ligands.

| | | GM1 | F-GM1 | $LOS_{GM1}$ | $G_{D1b}$ | Lipid $A_P$ |
|---|---|---|---|---|---|---|
| | | (Absorbance $_{492\ nm}$ by dilution of 1:20,000$^a$ $^{or}$1:5,000$^b$) | | | | |
| | $IC_{50}$ GM1 (pmol/mL) | 1.032 ± 0.072$^a$ | 0.988 ± 0.054$^a$ | 0.832 ± 0.066$^a$ | 0.789 ± 0.092$^a$ | 0.398 ± 0.103$^b$ |
| | | (Inhibition percent at $IC_{50}$ GM1) | | | | |
| $P_{GM1}$-1 | 38.0 | 50$^c$ | 45.8 | 50.8 | 39.9 | 0 |
| $P_{GM1}$-2 | 46.1 | 50 | 52.1 | 47.9 | 21.9 | 0 |
| $P_{GM1}$-3 | 9.6 | 50 | 43.9 | 52.1 | 37.9 | 0 |
| $P_{GM1}$-4 | 77.4 | 50 | 62.1 | 51.1 | 18.9 | 0 |
| $P_{GM1}$-5 | 34.4 | 50 | 52.1 | 50.0 | 39.8 | 0 |
| $P_{GM1}$-6 | — | 0 | 0$^d$ | 0$^d$ | 0$^d$ | 0$^d$ |

$^c$= means of 4 values;
$^d$= treatment with 100 pmol/mL of $P_{GM1}$-6.

At the concentration of $IC_{50}$, these peptides showed that the inhibitory activity for fucosyl-GM1 and $LOS_{GM1}$ was similar to that for GM1, but that for GD1b was significantly lower. The inhibitory activity of the six peptides on binding of GM1 with anti-GM1 rabbit antibody (anti-GM1Ab) was also tested (Table 4).

TABLE 4

Inhibitory activity of peptides on anti-GM1 antibodies.

| | | $Ab_{GM1}$-1 | $Ab_{GM1}$-2 | $Ab_{GM1}$-3 | $Abe_{GM1}$-4 | $Ab_{GM1}$-5 |
|---|---|---|---|---|---|---|
| | | (Absorbance$_{492\ nm}$ by dilution of 1:500) | | | | |
| | $IC_{50}$ $Ab_{GM1}$-1 (pmol/mL) | 0.891 ± 0.061 | 0.993 ± 0.074 | 0.671 ± 0.081 | 0.652 ± 0.056 | 0.798 ± 0.073 |
| | | (Inhibition percent at $IC_{50}$ $Ab_{GM1}$-1) | | | | |
| $P_{GM1}$-1 | 273.1 | 50$^a$ | 27.1 | 0 | 72.1 | 44.6 |
| $P_{GM1}$-2 | — | 0$^a$ | 32.1$^b$ | 65.7$^a$ | 15.1$^a$ | 0$^b$ |
| $P_{GM1}$-3 | 75.6 | 50 | 62.1 | 42.5 | 30.3 | 59.1 |
| $P_{GM1}$-4 | 175.3 | 50 | 70.1 | 12.6 | 33.9 | 0 |
| $P_{GM1}$-5 | 481.2 | 50 | 0 | 12.1 | 0 | 32.9 |
| $P_{GM1}$-6 | 293.4 | 50 | 45.1 | 0 | 55.1 | 18.7 |

$^a$= means of 4 values;

$^b$= treatment with 500 pmol/mL of $P_{GM1}$-2.

$Ab_{GM1}$-1 is from lot # 431A; $Ab_{GM1}$-2 is from lot # 431B; $Ab_{GM1}$-3 is from lot # 101J; $Ab_{GM1}$-4 is from lot # 104H; $Ab_{GM1}$-5 is from lot # 105T.

Unlike CTB-binding, inhibition of anti-GM1Ab required higher concentrations of peptides to reach their $IC_{50}$ values. Interestingly, one of the six peptides inhibited binding of GM1 with anti-GM1Ab, but not with CTB, while another one showed the opposite effect. Despite considerable variations in binding mode and affinity, the studies revealed that some of the peptides selected using CTB could serve as effective inhibitors for binding of GM1 with anti-GM1Ab. The peptides were also tested for inhibitory activity on other gangliosides binding to antibodies (Table 5).

TABLE 5

Inhibitory activity of peptides on other gangliosides binding to antibodies.

| | $IC_{50}$ $Ab_{GM1}$-1 (pmol/mL) | GM1/ $Ab_{GM1}$-1 | GM2/ $Ab_{GM2}$ | GM4/ $Ab_{GM4}$ | GD1a/ $Ab_{GD1a}$ | GD1b/ $Ab_{GD1b}$ | GD3/ $Ab_{GD3}$ | F-GM1/ $Ab_{F\text{-}GM1}$ | SGPG/ $Ab_{SGPG}$ |
|---|---|---|---|---|---|---|---|---|---|
| | | (Absorbance$_{492\ nm}$) | | | | | | | |
| | | 0.891 ± 0.061 | 0.453 ± 0.074 | 0.371 ± 0.091 | 0.345 ± 0.091 | 0.711 ± 0.056 | 1.311 ± 0.087 | 0.491 ± 0.055 | 0.698 ± 0.0591 |
| | | (Inhibition percent at $IC_{50}Ab_{GM1}$ − 1) | | | | | | | |
| $P_{GM1}$-1 | 273.1 | $50^b$ | 11.2 | 0 | 0 | 32.1 | 0 | 42.1 | 0 |
| $P_{GM1}$-2 | — | $0^b$ | $0^b$ | $0^b$ | $0^b$ | $23.6^b$ | $0^b$ | $0^b$ | $0^b$ |
| $P_{GM1}$-3 | 75.6 | 50 | 0 | 0 | 0 | 0 | 0 | 0 | 0 |
| $P_{GM1}$-4 | 175.3 | 50 | 0 | 0 | 0 | 12.1 | 0 | 25.7 | 0 |
| $P_{GM1}$-5 | 481.2 | 50 | 6.5 | 0 | 0 | 0 | 0 | 0 | 0 |
| $P_{GM1}$-6 | 293.4 | 50 | 0 | 0 | 0 | 8.9 | 0 | 23.4 | 0 |

$^a$= means of 4 values;

$^b$= treatment with 500 pmol/mL of $P_{GM1}$-2;

$Ab_{GM1}$-1 is from lot # 431A; $Ab_{GM2}$ is from lot # D710-2; $Ab_{GM4}$ is from lot # GMR6; $Ab_{GD1a}$ is from lot # 109H; $Ab_{GD1b}$ is from lot # D710-6; $Ab_{GD3}$ is from lot # R24; $Ab_{F\text{-}GM1}$ is from lot # G351; $Ab_{SGPG}$ is from lot # D710-5.

Further studies are being performed that employ the peptides in neutralizing pathogenic anti-GM1 Ab in patients with GBS.

Example II

Functional Inhibition of Cholera Toxin-Induced cAMP Production in Caco Cells by Peptide Mimics P3

Methods

Cells

Caco-2 cell line was established from human colorectal adenocarcinoma. Cells were maintained at 37° C. in a 5% $CO_2$ and 95% air atmosphere with DMEM medium containing 10% fetal bovine serum supplemented with penicillin (100 units/mL), and streptomycin (100 μg/mL). The medium were renewed every 5 to 6 days, and the cells were subcultured and harvested by trypsinization at the time of confluence.

cAMP Assay

Caco-2 cells ($7.0\times10^5$ cells/2 mL medium) were seeded into 6-well microtiter plates coated with poly-L-ornithine (0.1%) in 10% serum-DMEM medium. One week later, the cells were washed twice with PBS buffer, and exposed for 30 min to 0.5 μg/mL of GM1/2.5 mM HEPES buffer or in the absence of GM1. Subsequently, the cells were washed twice, and then CT and 1 mM IBMX were added to cells in 2 mL of 0.01% BSA/2.5 mM HEPES buffer containing P3 (50 pmol/mL or 50 nmol/mL) or in the absence of P3. The cells were incubated at 37° C. for 6 hours, followed by washing twice and harvesting cells by cells. The cells were sonicated briefly in 1 mL of 0.1 NHCL, and the supernatants collected into micro-centrifuge tubes. The protein concentration of the supernatants was adjusted to 1.0 mg/mL by the protein assay of 10 μL of the supernatant. cAMP in the supernatants was quantified using a cAMP EIA kit (Cayman Chemical Company, Ann Arbor, Mich.).

Results

GM1-like peptide P3 has inhibiting activity. In the present study, P3 was tested for inhibitor effect on cholera toxin (CT)-stimulated cyclic AMP production in the cells.

Standard curve cAMP was shown in FIG. 1. The absorbance ratio % $B/B_0$ (Standard Bound/Maximum Bound) was calculated, and plotted for logarithm of the standard cAMP concentrations. The data points from the standard cAMP concentration were simulated by the following mathematical formula:

$$Y = \text{Bottom} + \frac{\text{Top} - \text{Bottom}}{1 + \left(\frac{X}{C50}\right)^H}$$

Where Y is % $B/B_0$; Bottom is the lowest observed value; Top is the highest observed values; H is the trend of the slope, described as steep or shallow; C50 is 50% $B/B_o$ of the spread (Top-Bottom). The curve-fitting resulted in convergent parameters: Top=106.2, Bottom=4.708, C50=7.383, H=0.6595. According to the above formula, sample cAMP concentrations (pmol/cell mg protein) were determined.

Figure 2:
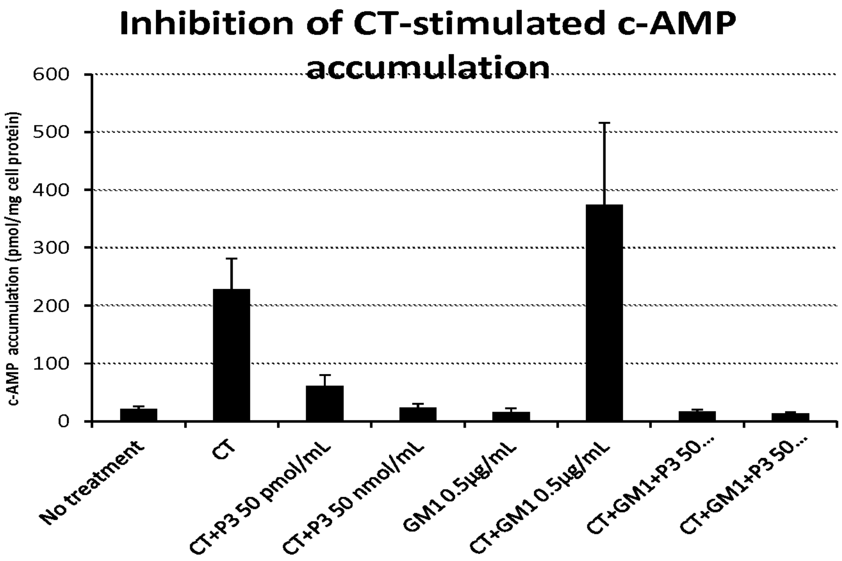
FIG. 2 is a bar graph showing the inhibition of CT-stimulated cAMP accumulation. Caco-2 cells were treated with cholera toxin (CT), CT plus P3, GM1, CT plus GM1, CT plus GM1 plus P3, or left untreated.

FIG. 2 showed the inhibition activity of P3 to CT-stimulated cAMP production in the Caco-2 cells. CT-treatment induced a remarkable production of cAMP (228.6 pmol/mg cell protein). P3-treatment at 50 pal/mL inhibited up to 27% of CT-induced cAMP production; at 50 nmol/mL, P3 completely suppressed CT-induced stimulation to the control level of cAMP. On the other hand, GM1-treatment did not influence cAMP production, whereas GM1 caused 1.6-fold amplification of CT-stimulated cAMP production.

P3 peptide mimics completely suppressed the CTX-induced cAMP production in Caco cells. In addition to cholera toxin, many other bacterial toxins bind to host cells for their activities, including *E. coli* heat-labile endotoxin (binds to GM1), verotoxin (Shiga toxin) (binds to globosides), and *Clostridium perfringens* (binds to GM1), etc. The use of peptide mimics is an effective general method for interfering with bacterial infection.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A peptide comprising SEQ ID NO:3 or a sequence comprising the amino-acids of SEQ ID NO:3 having one conservative substitution.

2. A peptide consisting of SEQ ID NO:3.

3. A composition comprising a peptide of claim 1.

4. The composition of claim 3, further comprising a therapeutic agent.

5. The composition of claim 3, further comprising a detectable agent.

6. The composition of claim 1, wherein the peptide is 50 amino acids or less.

* * * * *

SEQUENCE LISTING

```
<160> NUMBER OF SEQ ID NOS: 6

<210> SEQ ID NO 1
<211> LENGTH: 12
<212> TYPE: PRT
<213> ORGANISM: Artificial Sequence
<220> FEATURE:
<223> OTHER INFORMATION: synthetic construct; GM1-like peptide

<400> SEQUENCE: 1

Val Ser Trp Lys Thr Trp Phe Pro Asn Leu Ala Val
1               5                   10


<210> SEQ ID NO 2
<211> LENGTH: 12
<212> TYPE: PRT
<213> ORGANISM: Artificial Sequence
<220> FEATURE:
<223> OTHER INFORMATION: synthetic construct; GM1-like peptide

<400> SEQUENCE: 2

Tyr Ser Pro Phe His Lys Trp Phe Pro Ser Met His
1               5                   10


<210> SEQ ID NO 3
<211> LENGTH: 12
<212> TYPE: PRT
<213> ORGANISM: Artificial Sequence
<220> FEATURE:
<223> OTHER INFORMATION: synthetic construct; GM1-like peptide

<400> SEQUENCE: 3

Ile Pro Gln Val Trp Arg Asp Trp Phe Lys Leu Pro
1               5                   10


<210> SEQ ID NO 4
<211> LENGTH: 12
<212> TYPE: PRT
<213> ORGANISM: Artificial Sequence
<220> FEATURE:
<223> OTHER INFORMATION: synthetic construct; GM1-like peptide

<400> SEQUENCE: 4

Phe Pro Ala Trp Phe Thr Lys Leu Tyr Pro Arg Thr
1               5                   10


<210> SEQ ID NO 5
<211> LENGTH: 12
<212> TYPE: PRT
<213> ORGANISM: Artificial Sequence
<220> FEATURE:
<223> OTHER INFORMATION: synthetic construct; GM1-like peptide

<400> SEQUENCE: 5

Gln Ile Asn Thr Ala Lys Trp Trp Lys Thr His Phe
1               5                   10


<210> SEQ ID NO 6
<211> LENGTH: 12
<212> TYPE: PRT
<213> ORGANISM: Artificial Sequence
<220> FEATURE:
<223> OTHER INFORMATION: synthetic construct; GM1-like peptide
```

-continued

```
<400> SEQUENCE: 6

Asp Ala Ser Lys Ala Leu Arg Ser Ser Gly Met Pro
1               5                   10
```